US006875449B1

(12) United States Patent
Marriott et al.

(10) Patent No.: US 6,875,449 B1
(45) Date of Patent: Apr. 5, 2005

(54) CRYSTAL STRUCTURE

(75) Inventors: Christopher Marriott, London (GB); Gary Peter Martin, London (GB); Xian-Ming Zeng, Grays (GB)

(73) Assignee: Glaxo Wellcome, Inc., Research Triangle Park, NC (US)

(*) Notice: Subject to any disclaimer, the term of this patent is extended or adjusted under 35 U.S.C. 154(b) by 0 days.

(21) Appl. No.: 09/646,111

(22) PCT Filed: Mar. 24, 1999

(86) PCT No.: PCT/EP99/01966

§ 371 (c)(1),
(2), (4) Date: Nov. 20, 2000

(87) PCT Pub. No.: WO99/48475

PCT Pub. Date: Sep. 30, 1999

(30) Foreign Application Priority Data

Mar. 26, 1998 (GB) ............................................. 9806477

(51) Int. Cl.[7] ............................ A61L 9/04; A61K 9/14; A61K 9/16

(52) U.S. Cl. ........................... 424/489; 424/45; 424/46; 424/490; 424/493

(58) Field of Search ............................ 424/45, 46, 489, 424/490, 493, 499; 264/6, 8, 115, 118, 122

(56) References Cited

U.S. PATENT DOCUMENTS 4,725,387 A * 2/1988 Hirao et al. ................... 264/6
5,254,330 A * 10/1993 Ganderton et al. ........... 424/46
5,635,200 A * 6/1997 Douglas et al. ............. 424/441
5,747,445 A * 5/1998 Backstrom et al. ............ 514/4
6,129,905 A * 10/2000 Cutie .......................... 424/45
6,221,398 B1 * 4/2001 Jakupovic et al. .......... 424/489
6,309,623 B1 * 10/2001 Weers et al. .................. 424/45
6,627,597 B1 * 9/2003 Achanta et al. ............. 510/456

FOREIGN PATENT DOCUMENTS

WO WO 95/05805 * 3/1995
WO WO 95 05805 A 3/1995
WO 95/05805 * 3/1995
WO WO 96 23485 A 8/1996
WO WO 96/23485 * 8/1996
WO WO 96 38153 A 12/1996

OTHER PUBLICATIONS

G. Buckton et al., "The use of isothermal microcalorimetry in the study of changes in crystallinity of spray–dried salbutamol sulfate", International Journal of Pharmaceutics, Mar. 14, 1995, XP002110839.

* cited by examiner

*Primary Examiner*—Thurman K. Page
*Assistant Examiner*—S. Tran
(74) *Attorney, Agent, or Firm*—Bacon & Thomas

(57) ABSTRACT

A process for the production of crystals with controlled surface smoothness, size, shape and degree of crystallinity, compositions comprising such crystals, and the use of certain crystals, especially lactose, lactose monohydrate, fluticasone propionate, salmeterol xinafoate, salbutamol sulphate or ipratropium bromide in pharmaceutical compositions.

11 Claims, 3 Drawing Sheets

Figure 1:
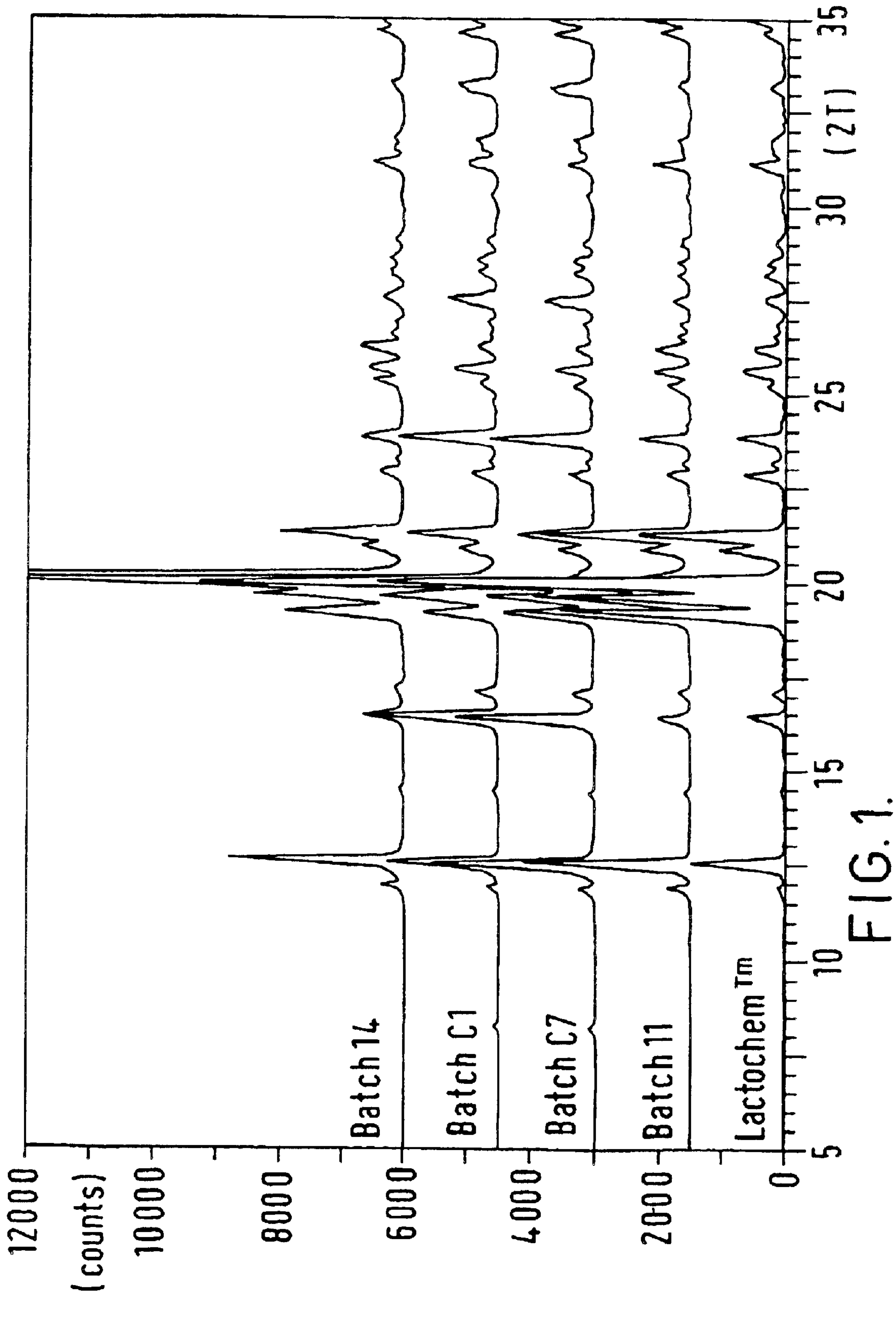

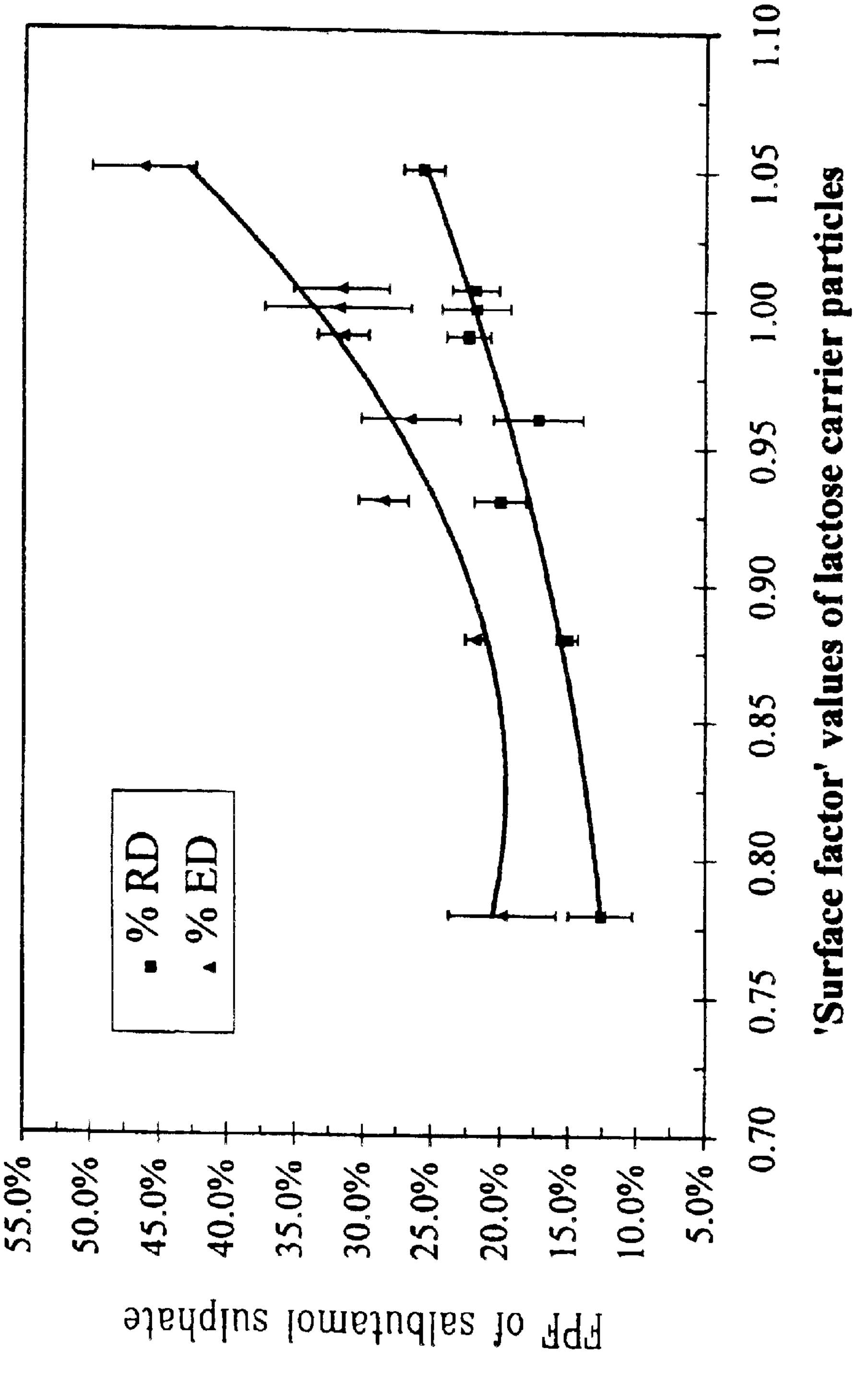
FIG. 2 The relationship between "surface factor" of lactose particles and the FPF of salbutamol sulphate aerosolised at 60 l $min^{-1}$ via a Cyclohaler™ (Error bars denote standard deviation, n ≥ 3).

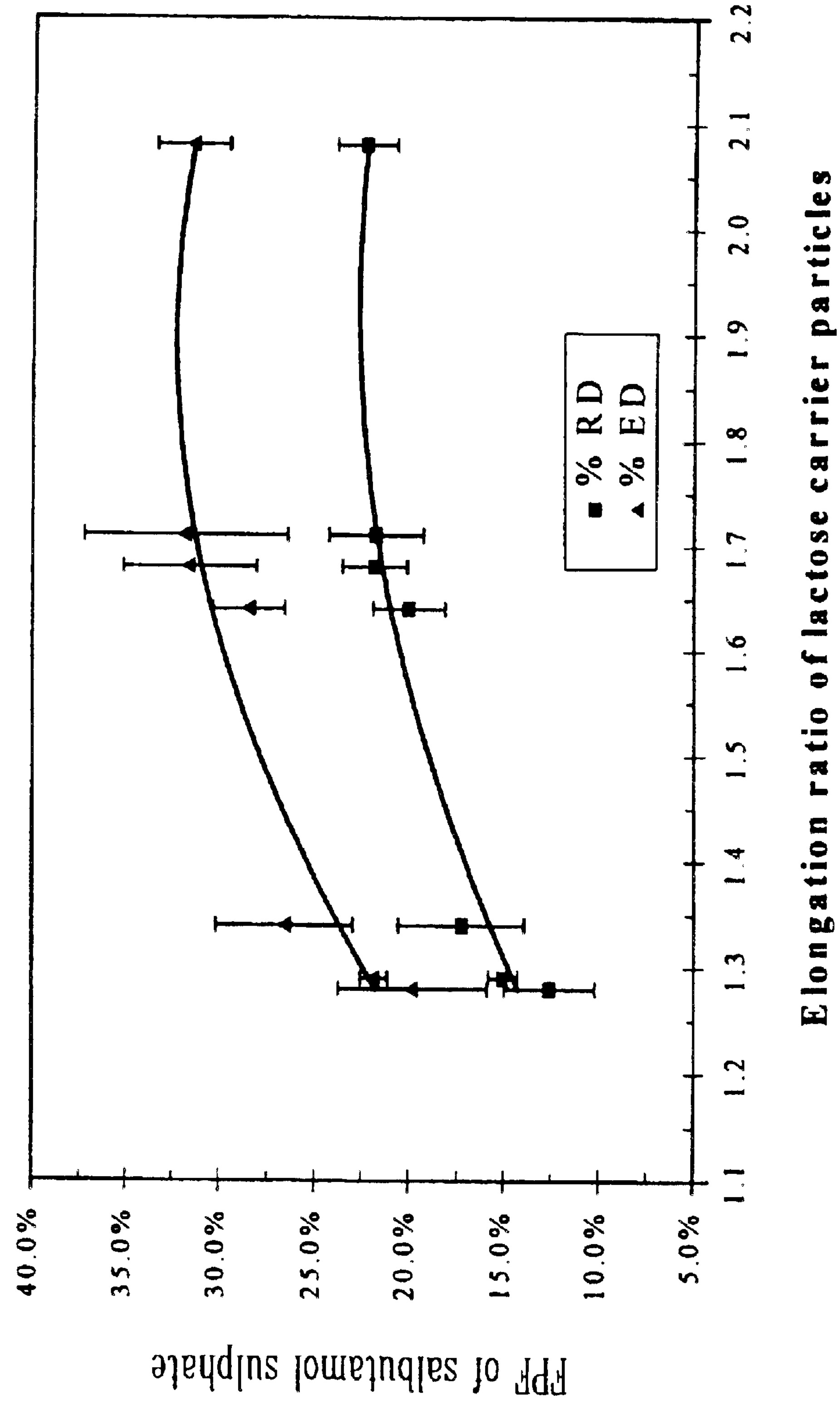
FIG. 3 The relationship between elongation ratio of lactose particles and the FPF of salbutamol sulphate aerosolised at 60 l $min^{-1}$ via a Cyclohaler™ (Error bars denote standard deviation, n ≥ 3).

CRYSTAL STRUCTURE

The present invention relates to an improved process for producing crystals with controlled surface smoothness, size, shape and degree of crystallinity. It also relates to compositions comprising such crystals and to the use of certain crystals to produce improved pharmaceutical compositions.

US5254330 discloses the fact that decreasing the rugosity of carrier particles facilitates redispersion of drug particles from compositions comprising carrier particles. The document describes a process for preparing particulate sugar crystals (preferred carrier particles). The process involves crystallisation from a saturated aqueous solution by the addition of at least an equal volume of a water immiscible organic solvent and a quantity of a solvent which is miscible with both water and the organic solvent. The solvent mixtures are preferably briskly agitated throughout the period of crystallisation and crystal growth. However, the carrier particles described in this document are of variable size (5 to 1000 micrometers).

Constant stirring is essential for the crystallisation of a substance from solution so as to avoid caking and the formation of other non-dispersible aggregates. However, mechanical stirring is likely to introduce random energy fluctuations in the solution, causing heterogeneous distributions of local concentrations. Such a hypothesis is supported by the phenomenon that a supersaturated solution can be induced to nucleate by a mere tap on the side of the vessel. The fluctuations in local concentrations induced by mechanical stirring may result in the heterogeneous growth of crystals since the growth rate is largely dependent upon the supersaturation of its surrounding solution. The heterogeneous growth will thus lead to the production of crystals with different particle size and irregular shapes, both of which have been commonly encountered when crystallisation is carried out under agitation. Further, mechanical stirring is known to induce secondary nucleation, which takes place in the presence of existing crystals (Larson, Chem. Eng. Commun, 1981, 12; 161). Thus, if a crystal is growing in a suspension under constant agitation, then, additional nuclei will continually be added to the crystal size distribution. Since the nucleation step also depletes the available supersaturation, in direct competition with the growth of the nuclei, the newly born crystals will grow to a lesser degree than the previously existent crystals. This will further widen the particle size distribution of final crystals. Therefore, mechanical stirring almost always results in the production of crystals with a wide size distribution with a large portion of small crystals and this can be seen from the particle size distribution of lactose prepared under constant stirring (Valle-Vega and Nickerson, J. Food Sci., 1977; 42; 1069–1072). Such a size distribution should be avoided in the preparation of lactose particles intended to be used as the carrier particles for inhalation aerosols since the majority of the particles are required to have a size range of 63–90 $\mu$m. The crystal shape is primarily determined by the supersaturation of the environment from which the crystals have been grown. Differences in supersaturation can be expected to result in the production of lactose crystals of different shape and surface textures. Crystals with such morphological properties would have inconsistent performance when used as carrier particles for any adhered drug particles.

Mechanical stirring (or agitation) also induces collisions between existing crystals, crystals and the wall of the vessel, and between the crystals and any agitation devices. The collision energy may cause small pieces of the crystals to be chipped away, which will then be distributed subsequently within the suspension. The chipped parts of crystals may act as stable embryos for new crystals to grow. Any chipped sites on the surface of broken crystals may also act as nuclei for new crystals to grow. Even if new crystals do not grow out of any chipped sites of a larger crystal, these fracture planes will undergo irregular growth, increasing the irregularity of both particle shape and surface textures of the affected crystal. Therefore, it may be advantageous to effect crystallisation from an undisturbed system, without any means of agitation, with a view to producing crystals with well defined morphology.

In order to grow crystals in an undisturbed system without the formation of any non-dispersible aggregates, crystals have previously been suspended in a gel (Mullin, in Crystallisation (Third edition) Butterworth-Heinemann Ltd., Oxford, 1993). The gel provides a protective barrier for the growing crystals and permits a steady diffusion of crystallising molecules. Without introducing any external turbulence to the solution, the gel can be expected to provide a homogeneous environment in which the crystals can grow and thus, overcome some of the major problems associated with the use of mechanical stirring. Since the crystals are in a stagnant suspension, individual crystals grow and mature without any fractures. Crystals prepared in this manner always have a more regular shape and a smoother surface than those obtained under mechanical stirring. Therefore, crystallisation from a gel has been widely used to obtain large, single crystals with well defined morphology. Further, secondary nucleation will occur to a much lesser extent in a gel than in the case of the solution under agitation. The inhibition of such nucleation may result in a narrower size distribution of the final particles. Monocrystals of $\alpha$-lactose monohydrate have been grown in a 0.7% w/w agar gel (Wong and Aulton, J. Pharm. Pharmacol., 1987; 39 (suppl.); 124P). However, the use of an agar gel may not prove to be suitable for the preparation of lactose particles intended to be used as a carrier for inhalation devices since agar is not a pharmaceutical excipient, and harvesting the bulk of crystals from an agar gel would prove to be problematic due to the relatively high consistency of the gel. Agar is also insoluble in most of the common organic solvents and this would make it very difficult to remove any adsorbed agar gel from the crystal surface.

Therefore, there is a need for a process which allows crystals to grow without any means of agitation during the crystallisation, and which provides large quantifies of crystals.

Surprisingly, we have now found a process which allows crystals to be prepared without mechanical stirring or agitation during the period of crystallisation and crystal growth. The crystals so produced overcome the disadvantages of large variations in size and shape, and have improved surface smoothness and degree of crystallinity, and have an elongated shape. There are many fields in which such crystals would be of particular advantage, for example carrier and drug particles for use in inhaled pharmaceutical formulations, and for additives in paints.

The present invention provides a crystallisation process, said process comprising:

a) dissolving the substance to be crystallised in a medium wherein the viscosity of the medium can be adjusted;

b) applying a means for adjusting the viscosity of the medium until a gel with an apparent viscosity in the range 25 to 90 Pa.s at a shear rate of 1 $s^{-1}$ is reached;

c) allowing crystal growth;

d) applying a means for adjusting the viscosity of the medium until a fluid with an apparent viscosity less than 25 Pa.s at a shear rate of 1 $s^{-1}$ is reached; and e) harvesting the crystals.

The means for adjusting the viscosity of the medium may be, for example temperature change ultrasound, thixotropicity, electro-rheology (application of an electric current), mechanical shear chemical additive (for example, sodium chloride or ethanol), or pH change. Preferably, the means for adjusting the viscosity of the medium is pH change.

The medium may be in the form of an aqueous or organic solution of a polymer. Preferably, the medium is an aqueous solution of a polymer.

The substance to be crystallised may be a drug substance, a chemical intermediate, an excipient, for example a carrier for drug particles suitable for use in an inhaled pharmaceutical composition, or may be, for example an additive for paint. Preferably, the substance to be crystallised is a water-soluble drug or a pharmaceutically acceptable carrier.

The crystals may be harvested by standard techniques known in the art. For example, the crystals may be collected by filtration, centrifugation or by decanting the supernatant and drying the crystals. Preferably, the harvested crystals are washed in a solvent in which the medium is soluble and the crystals are insoluble.

Numerous medicaments, especially those for the treatment of respiratory conditions such as asthma, are administered by inhalation. Since the drug acts directly on the target organ much smaller quantities of the active ingredient may be used, thereby minimising any potential side effects caused as a result of systemic absorption. The efficacy of this route of administration has been limited by the problems encountered in making appropriate and consistent dosages available to the lungs. The delivery systems currently available are pressurised metered dose inhalers, nebulisers and dry powder inhalers.

Metered dose inhalers require good co-ordination of actuation and inhalation in order to achieve consistent dose administration; this co-ordination may be difficult for some patients. Nebulisers are effective but are relatively expensive and bulky and as a result are mainly used in hospitals. A variety of dry powder inhalers have been developed and, since dry powder inhalers rely on the inspiratory effect of the patient to produce a fine cloud of drug particles, the co-ordination problems associated with the use of metered dose inhalers do not apply.

It has been found that medicaments for administration by inhalation should be of a controlled particle size in order to achieve maximum penetration into the lungs, preferably in the range of 1 to 10 micrometers in diameter. Unfortunately, powders in this particle size range, for example micronised powders, have a high bulk volume and have very poor flow characteristics due to the cohesive forces between the individual particles. These characteristics create handling and metering difficulties during manufacture of the medicament powder and, most importantly, adversely affect the accurate dispensing of the powder within the inhalation device. A number of proposals have been made in the literature to improve the fluidity of dry powder pharmaceutical formulations.

GB1520248 describes the preparation of soft pellets of finely powdered sodium cromoglycate which have satisfactory fluidity within the reservoir of the inhaler device but have sufficiently low internal coherence to break up into finer particles of medicament when introduced into the turbulent air stream in the mouthpiece of the device. Numerous other published patent applications suggest the use of carrier materials, for example GB1402423, particularly of coarser carriers with particles having sizes falling within a given range, for example GB1242211, GB1381872, GB1410588, GB1478020 and GB1571629. WO87/05213 describes a carrier which comprises a conglomerate of one or more solid water-soluble diluents and a lubricant, EP0260241 describes a lipid-based dry powder composition, and U.S. Pat. No. 5,143,126 describes a method of preparing flowable grain agglomerations of formoterol and lactose. Unfortunately the selection of the particle size of the drug and excipient and of the ratio of drug to excipient inevitably involves a compromise between adequate bulk and flow properties for metering and the desired redispersability of fine particle drug in the inhaled air flow.

Surprisingly, the process of the present invention can be used to produce crystals of drug or carrier with controlled size and shape, improved surface smoothness and degree of crystallinity, and an elongated shape. Such crystals overcome some of the formulation difficulties of compositions for inhalation.

In one preferred embodiment, the present invention provides a crystallisation process, said process comprising:

a) dissolving the substance to be crystallised in an aqueous solution of a medium wherein the viscosity of the medium is pH-dependent;
b) adjusting the pH of the medium until a gel with an apparent viscosity in the range 25 to 90 Pa.s at a shear rate of 1 $s^{-1}$ is reached;
c) allowing crystal growth;
d) adjusting the pH of the medium until a fluid with an apparent viscosity less than 25 Pa.s at a shear rate of is 1 $s^{-1}$ reached; and
e) harvesting the crystals.

Preferably the substance to be crystallised is a material suitable for use as a carrier or a drug in dry powder inhaler compositions. Preferred carriers include mono-saccharides, such as mannitol, arabinose, xylitol and dextrose and monohydrates thereof, disaccharides, such as lactose, maltose and sucrose, and polysaccharides such as starches, dextrins or dextrans. More preferred carriers comprise particulate crystalline sugars such as glucose, fructose, mannitol, sucrose and lactose. Especially preferred carriers are lactose and lactose monohydrate.

Preferably the average size of the particles of the carrier when distributed by mass is in the range 5 to 1000 micrometers, more preferably in the range of 50 to 250 micrometers, and most preferably in the range 50 to 100 micrometers. Typically at least 95% of the particles will be of a size which falls within this range.

Preferred drugs which may be administered in the powder compositions according to the invention, and which may also be crystallised according the present invention, include any drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin; isoetharine, tulobuterol, orciprenaline or (-)-4-amino-3,5-dichloro-α[[[6-[2-(2-pyridinyl)ethoxy]hexyl]-amino]methyl]benzenemethanol; diuretics, e.g. amiloride; anticholinergics, e.g. ipratropium, atropine or oxitropiurn; hormones, e.g. cortisone, hydrocortisone or prednisolone; xanthines, e.g. aminophylline, choline theophyllinate, lysine theophyllinate or theophylline; and therapeutic proteins and peptides, e.g. insulin or glucagon. It will be clear to a person skilled in the art that, were appropriate, the drugs may be used in the form of salts (e.g. as alkali metal or amine salts or as acid addition salts) or as esters (e.g. lower alkyl esters) or as solvates (e.g. hydrates) to optimise the activity and/or stability of the drug.

Particularly preferred drugs for administration using powder compositions in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate or (-)-4-amino-3,5-dichloro-α-[[[6-[2-(2-pyridinyl)ethoxy]hexyl]amino]methyl]benzenemethanol. Salmeterol, salbutamol, fluticasone propionate, beclomethasone dipropionate and physiologically acceptable salts and solvates thereof are especially preferred. Most preferred are fluticasone propionate, salmeterol xinafoate, salbutamol sulphate and ipratropium bromide.

Preferably the medium used to prepare the crystals intended to be used as a carrier in dry powder inhalation formulations will meet at least the following criteria. First, the medium should be suitable for use as a pharmaceutical ingredient for internal usage. Second, the medium should preferably be capable of being efficiently removed from the surface of the crystals so as not to affect any physicochemical properties of the crystals and, most importantly, to minimise the possibility of introducing such a compound to the respiratory tract. Third, the consistency or viscosity of the medium can be controlled such that after crystallisation, the bulk of crystals can be harvested easily without any vigorous treatment that might change the morphology of the crystals.

Preferably the polymer which comprises the medium is a Carbomer. Carbomers, a group of polyacrylic acid polymers cross-linked with either allylsucrose or allyl ethers of pentaerythritol, provide a medium that meets the aforementioned criteria. Carbomers have been widely used as suspending agents; emulsifying agents or tablet binders in pharmaceutical industry. Carbomer gels have also been employed as bioadhesive vehicles for mucoadhesive drug delivery formulations to prolong drug residence at the application sites. The viscosity of Carbomer gels is known to be dependent upon the polymer concentration (Barry and Meyer, Int. J. Pharm. 1979; 2; 1–25) and therefore, it is possible to obtain a minimal viscosity that can suspend the crystals without substantially inhibiting crystal growth. The viscosity of Carbomer gel changes reversibly with the pH value of the solution (Barry and Meyer, Int. J. Pharm, 1979; 2; 2740). Carbomers disperse in water to form acidic colloidal solutions of low viscosity which, when neutralised, produce highly viscous gels. The viscosity reaches a maximum at pH 6–11 but is considerably reduced if the pH is less than 3 or greater than 12. Therefore, the crystallisation can be carried out in a neutralised Carbomer gel. After which, the gel can be converted to a fluid by acidification such that the crystals may be readily harvested. In order to remove medium from the surface of the crystals, a solvent in which a Carbomer is soluble but the crystals are insoluble is required. Carbomers are soluble in both ethanol and glycerine, whereas the preferred crystals, lactose, are insoluble in these solvents. Therefore, any adsorbed Carbomer residue on lactose crystals may be easily removed by washing the crystals with either ethanol or glycerine without substantially changing the morphology of the crystals.

The pH of the medium may be adjusted by the addition of an aqueous base, for example it may be raised by the addition of aqueous sodium hydroxide solution, or it may be lowered by the addition of an aqueous acid, for example it may be lowered by the addition of hydrochloric acid.

Most preferably the medium is a Carbopol 934™ gel. Preferably the gel is an aqueous dispersion of Carbopol 934™ at a concentration of at least 0.4% w/w. Preferably, the concentration of Carbopol 934™ is in the range 0.4–0.8% w/w.

Preferably, the pH of the Carbopol 934™ gel is initially adjusted to be in the range pH 6.5–7.5, providing an apparent viscosity in the range 25–90 Pa.s at a shear rate of $1s^{-1}$, depending on the concentration. Preferably, the gel has a static yield value in the range 0.14–2.81 Pa for step b) of the process, to prevent crystals in the size range 50–1000 μm from sedimentation.

Preferably, after the crystal growth the pH of the Carbopol 934™ gel is adjusted to be in the range pH 3–3.5, providing a fluid. Preferably, the fluid has a static yield value <0.14 Pa.

It will be understood by those skilled in the art that other Carbomers may be used in the present invention, with concentration and pH parameters determinable by methods known in the art.

Preferably crystal growth is monitored, for example by use of an optical microscope, until the majority of the crystals have grown to a size in the range 50–125)μm, more preferably 63–90)μm.

In one aspect, the present invention provides crystals prepared according to the process as hereinbefore described. Preferably, the crystals are lactose monohydrate crystals.

When the medium is a Carbomer, preferably the harvested crystals are washed in a solvent in which the Carbomer is soluble and the crystals are insoluble, for example ethanol or glycerine.

In a further aspect, the present invention provides crystals obtainable by the process as hereinbefore described. Preferably, the crystals are lactose monohydrate crystals.

Crystals, for example lactose monohydrate crystals, prepared according to the process of the present invention, have a significantly higher mean elongation ratio and "surface factor" (see Table 3), and an improved degree of crystallinity (see Table 4) and flowability (significantly smaller angle of slide, see Table 5) than crystals prepared by the constant stirring technique.

Accordingly, one aspect of the present invention provides lactose monohydrate crystals having an elongation ratio of 1.58±0.33 and a size in the range 63–90 μm.

Surprisingly, we have found that crystals having high elongation ratios may, when employed as carrier particles in powder compositions suitable for inhalation, increase the fine particle fraction (FPF) of the medicament being carried, compared to crystalline carrier particles with lower elongation ratios (see Table 6). Since formulations that produce a higher FPF can be expected to deliver a higher fraction of medicament to the lower airways than those which produce a lower FPF, crystals with a higher elongation ratio provide advantageous formulations when employed as carrier particles.

Accordingly, the present invention provides use of carrier particles, preferably to lactose monohydrate crystals, with an elongation ratio in the range 1.55–2.20, preferably in the range 1.60–2.10, in the manufacture of powder formulations for inhaled use with improved drug fine particle fractions.

Elongated carrier particles, including crystals prepared according to the present invention, may be used to form pharmaceutical powder compositions suitable for inhalation with advantageous properties. Such compositions enable improved redispersion of drug particles.

Accordingly, one aspect of the present invention provides a pharmaceutical composition comprising elongated carrier particles, preferably elongated lactose monohydrate crystals, preferably in the form of elongated lactose monohydrate crystals prepared according to the process of the present invention, and particulate drug. The composition may optionally comprise a further pharmaceutically acceptable diluent or carrier.

Preferably the pharmaceutical composition comprises lactose monohydrate crystals having an elongation ratio in the range of 1.55–2.20, preferably 1.60–2.10.

The pharmaceutical composition may usefully additionally comprise any particulate drug suitable for administration by inhalation, such as those mentioned hereinbefore. It will be appreciated by those skilled in the art that the compositions according to the invention may, if desired, contain a combination of two or more active ingredients. Drugs may be selected from suitable combinations of the drugs mentioned hereinbefore. Thus, suitable combinations of bronchodilatory agents include ephedrine and theophylline, fenoterol and ipratropium, and isoetharine and phenylephrine formulations.

Other compositions may contain bronchodilators such as salbutamol (e.g. as the free base or as the sulphate salt), salmeterol (e.g. as the xinafoate salt) or isoprenaline in combination with an anti-inflammatory steroid such as a beclomethasone ester (e.g. the dipropionate) or a fluticasone ester (e.g. the propionate) or a bronchodilator in combination with an antiallergic such as cromoglycate (e.g. the sodium salt). Combinations of isoprenaline and sodium cromoglycate, salmeterol and fluticasone propionate, or salbutamol and beclomethasone dipropionate are especially preferred.

The final powder composition desirably contains 0.1 to 90% w/w, preferably 0.5 to 75% w/w, especially 1–50% w/w, of drug relative to the weight of the carrier particles.

Once formed, the carrier particles may be admixed with microfine particles of one or more medicaments, optionally together with one or more conventional pharmaceutically acceptable ingredients, using conventional techniques to prepare the powder compositions according to the invention.

The compositions according to the invention optionally contain one or more conventional pharmaceutically acceptable ingredients such as diluents and flavouring agents. The particle size of any such ingredients will preferably be such as to substantially prevent their inhalation into the bronchial system upon administration of the powder composition, desirably in the range of 50 to 1000 micrometers.

The final composition desirably contains 0.1 to 90% w/w, preferably 2 to 20% w/w of medicament and 10 to 99.9% w/w, preferably 50 to 99% w/w of carrier particles.

The compositions according to the invention may conveniently be filled into a bulk storage container, such as a multi-dose reservoir, or into unit dose containers such as capsules, cartridges or blister packs, which may be used with an appropriate inhalation device, for example as described in GB2041763, WO91/13646, GB1561835, GB2064336, GB2129691 or GB2246299. Such inhalers which contain a composition according to the invention are novel and form a further aspect of the invention. The compositions of the invention are particularly suitable for use with multi-dose reservoir-type inhaler devices in which the composition is metered, e.g. by volume from a bulk powder container into dose-metering cavities. The lower limit of powder delivery which may be accurately metered from a multi-dose reservoir-type inhaler device is in the region of 100 to 200 micrograms. The formulations of the present invention are therefore particularly advantageous for highly potent and hence low dose medicaments which require a high ratio of excipient for use in a multi-dose reservoir-type device.

Dry powder inhalers are designed to deliver a fixed unit dosage of medicament per actuation, for example in the range of 10 to 5000 micrograms medicament per actuation, preferably 25 to 500 micrograms.

Administration of the compositions of the present invention may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicament are employed the dose of each component of the combination will in general be that employed for each component when used alone. Typically, administration may be one or more times, for example from 1 to 8 times per day, giving for example 1, 2, 3 or 4 unit doses each time.

Thus, for example, each actuation may deliver 25 micrograms salmeterol, 100 micrograms salbutamol, 25, 50, 125 or 250 micrograms fluticasone propionate or 50, 100, 200 or 250 micrograms beclomethasone dipropionate.

The present invention further provides the use of lactose monohydrate crystals, as hereinbefore defined, in the preparation of a pharmaceutical composition.

The present invention is illustrated by the following Examples.

EXAMPLES

Example 1

Preparation of Lactose Monohydrate Crystals Using the Constant Stirring Technique One-step crystallisation from aqueous solution—A predetermined amount of lactose (Lactochem™, Borculo Whey Ltd., Chester, UK) was dissolved in 100 ml distilled water at 80° C. After filtration through a Whatman filter paper (<0.45μm), the solution was transferred to a 150 ml glass beaker which had been placed in either an ice bath or a water bath at 40° C. The solution was stirred at 500 rpm (Heidolph Overhead Stirrer, Fisons Laboratory Instruments, UK) with a 4 blade (1×3 cm) stirrer which was situated 2 cm above the bottom of the container. After the crystallisation was allowed to continue for a predetermined period of time, the crystals were filtered and washed sequentially with 60% (v/v) and absolute ethanol, respectively. The crystals were allowed to dry at room temperature overnight before drying in a vacuum oven at 70° C. for 3 h. After a small amount of sample (about 0.5 g) was taken from each batch of lactose for the measurement of particle size, shape and surface smoothness, the remaining lactose crystals were poured into a 90 μm sieve which had been placed upon a 63 μm sieve. The particles were then sieved manually and slowly for 1 h so as not to rupture any crystals. The particles were divided into 3 size fractions (<63, 63–90 and >90 μm), which were collected and weighted separately. The lactose crystals thus obtained (batches 1 to 11) were transferred to a sealed vial and placed into a desiccator over silica gel until required for further investigation. The samples obtained are given in Table 1 below.

Two stage crystallisation from aqueous solution—Lactochem™ lactose (200 g) was dissolved in 200 ml distilled water at about 90° C. The solution (about 320 ml) was filtered while still hot through a Whatman filter paper (0.45 μm). It was then transferred to a 500 ml glass beaker and stirred at 500 rpm with a 4 blade (1×3 cm) stirrer which was situated 2 cm above the bottom of the container. Lactose was then allowed to crystallise under constant stirring at room temperature at 500 rpm for 2.5 h. The crystals (A) were filtered and the mother liquor was placed back into the beaker and allowed to crystallise further for 16 h to obtain crystals (B). Batches A and B were washed with 60% (v/v) and absolute ethanol, respectively, and were allowed to dry at room temperature overnight. The lactose crystals were poured into a 90 μm sieve which had been placed upon a 63μm sieve. The particles were then sieved manually and slowly for 1 h so as not to rupture any crystals. Batch (A) was classified into batches 13 and 14, which had a particle size range from 63–90 μm and <63μm respectively. Batch (B) was classified into batches 15 and 16, which had a particle size range from 63–90 cm and <63 μm respectively. The crystals were then dried in a vacuum oven at 70° C. for 3h. The lactose crystals thus obtained (batches 13 to 16) were transferred to a sealed vial and placed into a desiccator over silica gel until required for further investigation. The samples obtained are in Table 1a below.

concentrations) under constant stirring at 500 rpm to obtain a cloudy solution with a pH value of approximately 2.5. Sodium hydroxide solution (1 M) was then added dropwise to the solution, whilst stirring at about 800 rpm. The viscosity and clarity of the solution increased with pH, until it became a clear homogenous gel at approximately pH 4.5. After then, the mixer was not sufficiently powerful to disperse the gel and hence, the mixing was continued manually with a spatula. The addition of the neutralising agent (NaOH) was continued so as to obtain pH 7. The gel was then centrifuged at 3000 rpm for about 10 min so as to remove any entrapped air bubbles and insoluble particles. The gel was finally placed in the dark until the majority of the crystals had grown to the size range of 63–90 μm, which was estimated by an optical microscope, the gel was adjusted to pH 3–3.5 with hydrochloric acid (1 M) to obtain a fluid. The crystals were allowed to settle for about 10 min. After decanting the supernatant, the crystals were routinely washed with 60% ethanol twice and absolute ethanol three times. The crystals were finally allowed to dry at room temperature after which, a small amount of sample (about 0.5 g) was taken from each batch of lactose, the remaining lactose crystals were poured into a 90 μm sieve which had been placed upon a 63 μm sieve. The particles were then sieved manually and slowly for 1 h so as not to rupture any crystals. The particles were thus divided into 3 size fractions (<63, 63–90 and >90 μm) which were collected and weighted separately. The classified lactose crystals were dried in a vacuum oven at 70° C. for 3 h before transferring to sealed vials, which were then placed in a desiccator over silica gel.

TABLE 1

| | Lactose | T | Time | Diameter ($d_w$) ± | % Particle (μm) | | | |
|---|---|---|---|---|---|---|---|---|
| Batch No | (% w/w) | (° C.) | (h) | SD (μm) | <63 | 63–90 | >90 | Shape |
| 1 | 33 | 40 | 12 | 83.6 ± 12.8 | 13.9 | 45.8 | 40.3 | Tomahawk |
| 2 | 33 | 40 | 24 | 115.8 ± 14.6 | 5.6 | 15.1 | 79.3 | Tomahawk |
| 3 | 33 | 0 | 24 | 100.3 ± 18.9 | 15.2 | 17.2 | 67.6 | Irregular |
| 4 | 43 | 0 | 5 | 94.4 ± 13.4 | 19.6 | 21.8 | 56.6 | Irregular |
| 5 | 43 | 0 | 12 | 104.5 ± 14.8 | 14.9 | 23.2 | 61.9 | Irregular |
| 6 | 43 | 40 | 5 | 103.8 ± 20.6 | 14.4 | 21.6 | 64.0 | Tomahawk |
| 7 | 33 | 0 | 12 | 63.7 ± 9.4 | 33.0 | 40.0 | 26.8 | Irregular |
| 8 | 43 | 40 | 12 | 100.6 ± 15.3 | 24.5 | 17.9 | 57.6 | Pyramid |
| 9 | 50 | 40 | 3 | 88.8 ± 13.8 | 27.5 | 31.9 | 40.6 | Prism |
| 10 | 60 | 40 | 0.3 | 76.4 ± 15.7 | 33.8 | 46.3 | 19.9 | Elongated |
| 11 | 60 | 40 | 1.5 | 91.8 ± 17.9 | 26.3 | 27.6 | 46.1 | Elongated |

TABLE 1a

| Batch No | Diameter ($d_{SV}$) (μm) |
|---|---|
| 13 | 104.7 |
| 14 | 68.6 |
| 15 | 93.0 |
| 16 | 65.3 |

Example 2

Preparation of Lactose Monohydrate Crystals Using Carbomer Gel

A predetermined amount of distilled water was agitated at about 500 rpm with a 4-bladed stirrer (1×3 cm) which was situated 2 cm above the bottom of a 500 ml beaker. The required amount of Carbopol 934™ (B F Goodrich Chemical Co., Cleveland, Ohio, USA) with an average molecular weight of approximately 3,000,000, was added into the vortex. When all the Carbopol was dispersed, the liquid was allowed to stand overnight in the dark so as to ensure maximum dissolution of the polymer. A cloudy, colloidal solution of low viscosity was obtained, the pH of which was about 3.2. The required amount of Lactochem™ lactose was then dissolved in the Carbopol solution at an elevated temperature (<90° C., depending upon the final lactose Crystallisations of the lactose from Carbopol 934™ gels were carried out under different conditions by means of altering the crystallisation time and the concentrations of either lactose or Carbopol gels (Table 2). Three batches of lactose crystals were prepared under each of the seven conditions listed in Table 2 but in each case the 3 batches were then mixed to prepare final batches of lactose, which were labelled as Car 1 to Car 7, respectively. The 63–90 μm fraction of batches Car 1 to Car 7 were labelled as C1 to C7, respectively. Lactose crystals from batch Car 1 were further classified into fractions <63; 90–125 and >125 μm, which in turn were labelled as C8; C9 and C10 respectively. Batch C7 was washed directly with 100% ethanol rather than prewashing with 60% v/v ethanol as described above.

The samples obtained are given in Table 2 below:

TABLE 2

| Batch No. | Lactose (% w/v) | Carbopol (% w/v) | Crystal time (h) | Mean Size ($\mu$m) | % Particle ($\mu$m) <63 | 63–90 | >90 |
|---|---|---|---|---|---|---|---|
| Car 1 | 43.0 | 0.6 | 72 | 105.4 | 5.8 | 35.4 | 58.8 |
| Car 2 | 43.0 | 0.3 | 24 | 87.9 | 10.3 | 56.5 | 33.2 |
| Car 3 | 33.0 | 0.3 | 24 | 76.5 | 12.2 | 68.7 | 19.1 |
| Car 4 | 50.0 | 0.4 | 48 | 116.3 | 8.2 | 12.6 | 79.2 |
| Car 5 | 50.0 | 0.6 | 72 | 114.2 | 1.4 | 22.3 | 76.3 |
| Car 6 | 38 | 0.4 | 72 | 93.3 | 8.5 | 53.5 | 38.0 |
| Car 7 | 38 | 0.4 | 48 | 75.4 | 15.6 | 73.2 | 11.2 |

Example 3

The shape factor (Scir), elongation ratio (E) and surface factor (Srec) of the samples was calculated in the following manner:

A small amount of lactose particles was scattered on a microscope slide using a small brush ensuring that the particles deposited separately. The slide was then mounted on an optical microscope (Labophot-2, Nikon, Japan) and the images of the particles were transferred to an IBM compatible computer through a Nikon camera. Particle images were analysed automatically using analySIS 2.0 (SIS Image Analysis GmbH, Germany) and the following descriptors were employed to quantify the morphology of lactose crystals:

$$\text{Shape factor} = S_{cir} = \frac{4\Pi \text{ area}}{\text{perimeter}^2}$$

$$\text{Elongation ratio} = E = \frac{\text{Length}}{\text{Width}}$$

$$\text{Surface factor} = S_{rec} = S_{cir} \times \frac{(1+E)^2}{\Pi E}$$

All the particles that were projected onto the monitor were analysed and more than 100 particles were measured for each batch.

TABLE 3

| Crystallisation with Constant Stirring | | | | Crystallisation in Carbopol 934 ™ gels | | | |
|---|---|---|---|---|---|---|---|
| Batch No. | $S_{cir}$ | E | $S_{rec}$ | Batch No. | $S_{cir}$ | E | $S_{rec}$ |
| 1 | 0.74 | 1.39 | 0.97 | C1 | 0.76 | 1.58 | 1.02 |
| 2 | 0.74 | 1.39 | 0.97 | C2 | 0.70 | 1.61 | 0.94 |
| 3 | 0.60 | 1.28 | 0.78 | C3 | 0.68 | 1.59 | 0.91 |
| 4 | 0.68 | 1.29 | 0.88 | C4 | 0.73 | 1.85 | 1.02 |
| 5 | 0.72 | 1.30 | 0.93 | C5 | 0.76 | 1.55 | 1.01 |
| 6 | 0.69 | 1.64 | 0.93 | C6 | 0.71 | 2.03 | 1.02 |
| 7 | 0.74 | 1.34 | 0.96 | C7 | 0.68 | 1.78 | 0.94 |
| 8 | 0.72 | 1.37 | 0.94 | | | | |
| 9 | 0.78 | 1.63 | 1.05 | | | | |
| 10 | 0.68 | 2.08 | 0.99 | | | | |
| 11 | 0.73 | 1.71 | 1.00 | | | | |
| 13 | 0.65 | 1.79 | 0.90 | | | | |
| 14 | 0.65 | 1.55 | 0.87 | | | | |
| 15 | 0.69 | 1.81 | 0.96 | | | | |
| 16 | 0.72 | 1.54 | 0.96 | | | | |

Example 4

Degree of Crystallinity

X-ray powder diffraction (XRPD) patterns for different batches of lactose were performed (FIG. 1). All batches had similar XRPD patterns to α-lactose monohydrate (Brittain et al, Pharm. Res. 1991, 8, 963–973 and Sebhatu et al, Int. J. Pharm. 1994, 104, 135–144). However, different batches showed different peak intensities, which were indicative of different degrees of crystallinity of these lactose crystals.

X-ray powder diffractometry has been widely used to determine the degree of crystallinity of pharmaceuticals (Suryanarayanan, in Brittain HG (Ed), Physical Characterisation of Pharmaceutical Solids, Marcel Dekker, NY, 1995, 187–222). Some XRPD methods involve the demarcation and measurement of the crystalline intensity and amorphous intensity from the powder patterns (Nakai et al., Chem. Pharm. Bull. 30, 1982, 1811–1818) whilst others employ an internal standard such as lithium fluoride to measure the crystallinity of drugs. Therefore, it is not possible to calculate the absolute degree of crystallinity by the XRPD patterns in FIG. 1 since neither 100% amorphous lactose nor any internal standard was measured. However, since the degree of crystallinity is a function of either the integrated intensity (area under the curve) or the peak intensity (height), the relative degree of crystallinity of different samples of the same crystal forms may be compared by their peak intensity at the same diffraction angle. The relative degree of crystallinity (RDC) was defined as the ratio of the peak intensity of a given sample of a single polymorphic form to that of another specimen of the same polymorph which produced the greatest possible response (Ryan, J. Pharm. Sci. 75, 1986, 805–807). RDC may be employed to determine the rank order of crystallinity of different batches of lactose crystals. The integrated peak intensities at 2θ=12.5°, 16.5°, 23.8° and 27.5°, which are characteristic for α-lactose monohydrate, were determined by measuring the areas under the curve of the X-ray diffraction profiles. The RDC was calculated by dividing the sum of the four integrated peak intensities of each batch by that of batch C7 since this batch produced the greatest trace of X-ray diffraction. It can be seen from Table 4 that the degree of crystallinity decreases in the order of batch C7>batch C1>Lactochem™ lactose>batch 11>batch 14.

TABLE 4

Estimates of the integrated peak intensities (cm$^2$) of XRDPs and the relative degreee of crystallinity (RDC) of lactose crystals

| Angle (2θ) | Lactochem ™ | Batch 11 | Batch 14 | C1 | C7 |
|---|---|---|---|---|---|
| 12.5° | 0.72 | 0.70 | 0.41 | 0.58 | 0.81 |
| 16.5° | 0.11 | 0.88 | 0.10 | 0.67 | 0.68 |
| 23.8° | 0.16 | 0.11 | 0.16 | 0.45 | 0.40 |
| 27.5° | 0.04 | 0.07 | 0.07 | 0.19 | 0.17 |
| Sum | 1.03 | 0.96 | 0.74 | 1.89 | 2.06 |
| RDC (%) | 50.0 | 46.6 | 35.9 | 91.7 | 100 |

The lactose crystals prepared from Carbopol 934 ™ gels had a higher degree of crystallinity than lactose particles crystallised under conditions of constant mechanical agitation.

Example 5

Flowability

The angle of repose ($\theta_r$) for batches of lactose crystals was measured (at least in triplicate) by pouring a sample of crystals into a copper tube (2.65 cm×6.90 cm), which had been placed over a flat base with a diameter of 2.53 cm. After the powder heap reached a height of approximately 4 cm, the addition of powder was stopped and the copper tube was slowly lifted vertically off the base, on which a cone of powder was formed. The height of the cone was measured using a ruler and the $\theta_r$ calculated as:

$$\theta_r = \text{Tangent}^{-1}\left(\frac{hp}{r_b}\right)$$

where hp is the height (cm) of the powder heap and rb is the radius (cm) of the base.

The angle of slide ($\theta_s$) for batches of lactose crystals was measured, at least in triplicate, by placing lactose crystals (approximately 10 mg) on a stainless steel plane (6.55×7.00 cm). The plane was tilted by screwing a spindle vertically upwards below the plane. When the majority of the powder started to slide, the angle between the tilted plane and the horizontal base, $\theta_s$, was directly read from a protractor.

The results are listed in Table 5.

TABLE 5

The angle of repose and angle of slide of different batches of lactose crystals [mean (SD), n ≧ 3]

| Crystallisation with Constant Stirring | | | Crystallisation in Carbopol 934 ™ gels | | |
|---|---|---|---|---|---|
| Batch No. | $\theta_r$ (°) | $\theta_s$ (°) | Batch No. | $\theta_r$ (°) | $\theta_s$ (°) |
| 1 | 43 (1) | 50 (1) | C1 | 46 (1) | 48 (0) |
| 3 | 41 (1) | 47 (1) | C2 | 40 (0) | 43 (1) |
| 4 | 43 (1) | 50 (2) | C3 | 41 (2) | 45 (1) |
| 5 | | 46 (2) | C4 | 40 (1) | 45 (2) |
| 6 | 53 (1) | 62 (1) | C5 | 42 (2) | 48 (1) |
| 7 | 38 (0) | 43 (1) | C6 | 41 (0) | 43 (1) |
| 8 | 56 (2) | >90 | C7 | 43 (1) | 40 (1) |
| 9 | 37 (1) | 43 (1) | Lactochem ™ | 48 (2) | 50 (1) |
| 10 | 34 (1) | 38 (1) | | | |
| 11 | 32 (1) | 34 (1) | | | |
| 13 | 58 (1) | 74 (1) | | | |
| 14 | 60 (0) | >90 | | | |
| 15 | 57 (2) | 71 (0) | | | |
| 16 | 59 (1) | >90 | | | |

Table 5 shows that different batches of lactose exhibited different degrees of both the angle of repose ($\theta_r$) and the angle of slide ($\theta_s$). Lactose particles from batches 10 and 11 produced significantly ($p<0.01$) smaller values of $\theta_r$ or $\theta_s$, than the other batches of lactose, indicating that the former had higher flowability than the latter. The majority of lactose crystals from batches 10 and 11 had an elongated, cuboidal shape (Table 1). Elongated particles are known to build up open packings of high porosity. In flow, such particles tend to be oriented with their long axes in the direction of the flow and if such an orientation is achieved, these particles show less internal friction than more isometric particles (Neumann, Adv. in Pharm. Sci. 2, 1967, 181–221). Batches 14 and 16 produced the largest $\theta_r$ and these particles did not even slide off the plane that had been tilted to an angle of 90° to the horizontal, indicating that these two batches of lactose were highly cohesive and had poor flowability. This is likely to be attributable to the smaller mean diameter (approximately 65 μm) of batches 14 and 16 in comparison to the other batches of lactose (>90 μm) since powders of smaller particle size are known to produce larger $\theta_r$ due to their internal cohesiveness (Neumann, Adv. in Pharm. Sci. 2 1967, 181–221). Lactose particles prepared from Carbopol 934 gels showed more consistent values of $\theta_r$ (40–46°) and $\theta_s$ (40–48°) in comparison to crystals prepared using agitation and this is likely to be due to more effective control of their particle morphology. Further, the crystals prepared from Carbopol 934 gels appeared to have better flowability than the majority of the batches prepared under constant stirring since they had significantly ($p<0.01$) smaller values of 0 than the other batches of lactose (batches 1–8). The angle of repose differs from the angle of slide in that the former is determined by the least stable particles whilst the latter depends largely on the average conditions for the bulk of the powder (Hiestand, J. Pharm. Sci. 55, 1966, 1325–1344). Therefore, the angle of slide may correlate more closely with flow properties than the angle of repose.

Example 6

Deposition Profiles of Salbutamol Sulphate from Different Batches of Lactose Crystals Salbutamol sulphate and lactose were mixed in a ratio of 1:67.5, w/w in accordance with the ratio employed in the commercial "Ventolinl™" formulation. After drying in a vacuum over at 40° C. for 12 h, micronised salbutamol sulphate with mass median diameter 2.0 μm (Glaxo Wellcome Group Ltd., Ware, UK) (25 mg), was weighed into a 10 ml stoppered sample vial to which had been added one spatula full of lactose crystals. The vial was stoppered and placed on a Whirlymixer for 5 s. Then, more lactose particles (similar to the amount of the blend) was added to the vial and the blend was mixed on a Whirlymixer for another 5 s. This process was repeated until all the lactose (1.750 g) had been incorporated into the salbutamol sulphate/lactose blend to obtain a ratio of drug to carrier of 1 : 67.5, w/w. The stoppered vials were then placed in a Turbula mixer (Glen Creston Ltd., Middx, UK) and mixed for 30 min. The samples were then stored in a vacuum desiccator over silica gel until further required.

Ten samples were taken randomly from each batch. The sample (approximately 33 mg) was weighed accurately and the amount of salbutamol sulphate was measured by HPLC. The coefficient of variation of the drug content was employed to assess the homogeneity of the mixtures.

Hard gelatin capsules (Size 3, Rotacapsule™, Glaxo Wellcome Group Ltd., Ware, UK) were filled with 33.0±1.5 mg of the powder mixture so that each capsule contains 481±22 μg salbutamol sulphate, which was the unit dose contained in a Ventolin Rotacap™. The filling was performed manually.

Ethyl paraben was dissolved in the mobile phase to produce a solution with a concentration of 4 μg $ml^{-1}$.

An accurately weighed amount of salbutamol sulphate (20.0 mg) was transferred to a 100 ml volumetric flask, dissolved in the internal standard solution, and made up to volume to obtain a concentration of 0.2 mg ml-1 of salbutamol sulphate (solution A). 10.0 ml of solution A was pipetted into another 100 ml volumetric flask and diluted to volume with the internal standard solution to obtain a solution containing 20 μg $ml^{-1}$ salbutamol sulphate (solution B).

Aliquots of solution B (0.25, 0.50, 1.00, 2.00, 3.00, 4.00, 5.00, 6.00, 7.00 ml) were pipetted into 10 ml volumetric flasks and made up to volume using the internal standard solution to obtain a series of the standard solutions which contained drug concentrations of 0.5, 1.0, 2.0, 4.0, 6.0, 6.0, 10, 12 and 14 μg $ml^{-1}$ respectively. These standard solutions were employed to construct a calibration curve of drug concentration against the peak area ratios of drug to internal standard. The calibration was prepared on a daily basis and a calibration curve with $r^2>0.99$ was considered acceptable.

Approximately 33 mg of the powder mixture was accurately weighed and dissolved in the internal standard solution. After the solution had been sonicated in a water bath for 30 min, it was filtered through a millipore filter (Whatman membrane filters, 0.45 μm, nylon, Whatman Lab. Division, Kent, UK). 30 μl of the filtrate was injected into the HPLC.

No interference from the lactose carrier was observed. The concentration of salbutamol sulphate was calculated by interpolation using the previously constructed calibration curve.

HPLC mobile phase containing the internal standard (7 ml) was introduced into the upper stage and 30 ml of the same solvent into the lower stage of a twin stage liquid impinger. The capsule, to be tested, was placed in a commercially available inhaler (either Rotahaler™, Glaxo Wellcome, Ware, UK or Cyclohaler™, Pharbita BV, the Netherlands), which had been fitted into a moulded rubber mouthpiece attached to the throat piece of the impinger. Once the assembly had been checked and found to be airtight and vertical, the vacuum pump was switched on. After the pump had run for 5 s, the dose was released. the pump was allowed to run for another 7 s at 60±11 $min^{-1}$ following the release of the dose and it was then switched off. The capsule shells were removed from the inhaler device and the deposition test was repeated until six capsules has been actuated in the same manner. The inhaler body, capsule shells and mouth piece were washed 5 times with the mobile phase containing internal standard and the washing solution was made up to 100 ml with the same solvent. The sample thus obtained was used to measure the amount of drug retained in the inhaler device. The same process was carried out for both the upper and the lower stage of the twin-impinger. All the samples obtained were analysed for the concentration of salbutamol sulphate using HPLC.

The recovered dose (RD) was the sum of the drug collected in the inhaler device, upper and lower stages of the impinger, whilst the emitted dose (ED) was the amount of drug released from the inhaler device, i.e. the sum of drug collected at upper and lower stages of the impinger. However, fine particle dose (FPD) was defined as the amount of drug deposited in the lower stage of the impinger, which has a diameter less than the cut-off diameter of the upper stage of a twin-impinger (6.4 μm at an air flow rate of 60±11 $min^{-1}$). The fine particle fraction (FPF) was calculated as the ratio of the fine particle dose to either the recovered dose (FPF % RD) or the emitted dose (FPF % ED). The total recovery (% recovery) of the drug was assessed by the ratio of the recovered dose to the theoretical dose, the latter being the dose of salbutamol sulphate in the capsules. For example, the theoretical dose of salbutamol sulphate in one capsule was 481±22 μg, which was equivalent to the filling weight (33.0±1.5 mg) of lactose and salbutamol sulphate blends.

The mixtures were found to be homogenous with a coefficient of variation in salbutamol sulphate content of less than 2.2% (n=10).

The deposition data in Table 6 were calculated as one capsule per actuation at 60 l $min^{-1}$ via a Cyclohaler™. It can be seen that the recovered dose (RD) of salbutamol sulphate varied from 391 μg for the blend containing batch 9 lactose to 508 μg for the blend composed of batch 10 lactose, corresponding to a % recovery of between 81.2–105.5%. The drug recovery was reasonably satisfactory with an average recovery of 94.1% from all of the eight formulations investigated. The emission of drug from the inhaler device ranged from 55.6% for blends containing batch 9 lactose to 70.8% for blends containing batch 10 lactose, with an average drug emission of 66.5%, indicating that a large portion (33.5% RD) of the drug was retained in the inhaler device.

The blends containing batch 9, 10, 11 and Lactochem™ lactose produced a similar fine particle dose (FPD) of salbutamol sulphate, which was significantly higher ($p<0.01$) than that obtained from the blends which were composed of batch 3, 4 or 7 lactose. The blends containing batch 9 lactose produced the highest FPF in terms of both % RD (25.6%) and % ED (46.2%), which were more than twice the FPF of the formulations containing batch 3 lactose, the FPF of the latter being 12.6% RD or 19.8% ED. These batches of lactose particles had similar particle size but with different surface smoothness and particle shape. The differences in particle shape and surface texture of lactose carrier particles may account for the differences in the deposition of the drug since all the powders are composed of the same batch of salbutamol sulphate. The lowest values for FPF of drug, obtained using blends containing batch 3 or 4 lactose may be due to those batches having the roughest surfaces with the least elongated particle shape.

TABLE 6

Deposition of salbutamol sulphate from different batches of lactose in a twin-impinger after aerosolisation at 60 l $min^{-1}$ via a Cyclohaler ™ [mean (SD), n ≧ 3].

| Batch No. | RD (μg) | ED (μg) | FPD (μg) | FPF % RD | FPF % ED | Recovery % | Emission % |
|---|---|---|---|---|---|---|---|
| *Lact | 460 (20) | 320 (37) | 101 (12) | 21.8 (1.7) | 31.6 (3.5) | 95.7 (4.2) | 69.3 (6.0) |
| 3 | 432 (18) | 276 (15) | 54 (10) | 12.6 (2.4) | 19.8 (3.9) | 89.7 (3.8) | 63.8 (0.9) |
| 4 | 425 (24) | 294 (10) | 64 (2) | 15.1 (0.8) | 21.8 (0.7) | 88.3 (5.0) | 69.1 (1.7) |
| 6 | 454 (20) | 319 (14) | 91 (8) | 20.0 (1.9) | 28.5 (1.9) | 94.4 (4.1) | 70.2 (1.9) |
| 7 | 398 (28) | 257 (34) | 69 (18) | 17.2 (3.3) | 26.6 (3.6) | 82.7 (5.9) | 64.6 (4.0) |
| 9 | 391 (48) | 217 (29) | 101 (18) | 25.6 (1.5) | 46.2 (3.8) | 81.2 (10.0) | 55.6 (2.5) |
| 10 | 508 (13) | 359 (5) | 113 (5) | 22.3 (1.6) | 31.5 (1.9) | 105.5 (2.7) | 70.8 (0.8) |
| 11 | 450 (35) | 344 (40) | 108 (7) | 21.8 (2.5) | 31.9 (5.4) | 103.9 (7.3) | 68.7 (3.7) |

*Lact = Lactochem ™ lactose

The surface smoothness and particle elongation have been quantified previously using the terms "surface factor" and elongation ratio, respectively. FIGS. 2 and 3 show these shape and surface descriptors of lactose carrier particles against the drug FPF of the corresponding blends.

From FIGS. 2 and 3, it can be seen that increasing the surface smoothness of lactose carrier particles, as expressed by the "surface factor", generally resulted in an increase in the FPF of salbutamol sulphate in terms of either % RD or % ED. Interestingly, increasing the elongation ratio of the lactose carrier particles also resulted in an increase in the FPF of salbutamol sulphate (FIG. 3). These results suggest that apart from surface smoothness, the elongation of carrier particles may also play an important role in determining the FPF of the drug.

What is claimed is:

1. A crystallisation process for lactose or lactose monohydrate comprising:

a) dissolving lactose or lactose monohydrate in an aqueous solution of a Carbomer;

b) applying a means for adjusting the viscosity of the aqueous solution of a Carbomer until a gel with an apparent viscosity in the range 25 to 90 Pa.s at a shear rate of 1 $s^{-1}$ is reached;

c) allowing crystal growth;

d) applying a means for adjusting the viscosity of the aqueous solution of a Carbomer until a fluid with an apparent viscosity less than 25 Pa.s at a shear rate of 1 $s^{-1}$ is reached; and e) harvesting the crystals.

2. A crystallisation process as claimed in claim 1, wherein the means for adjusting the viscosity of the aqueous solution of a Carbomer is temperature change, ultrasound, thixotropicity, electro-rheology, mechanical shear, chemical additive, or pH change.

3. A crystallisation process as claimed in claim 2, wherein the means for adjusting the viscosity of the aqueous solution of a Carbomer is pH change.

4. A crystallisation process as claimed in claim 1, wherein the crystals are harvested by means of collection by filtration.

5. A crystallisation process as claimed in claim 1, wherein the process comprises:

a) dissolving lactose or lactose monohydrate to be crystallised in an aqueous solution of a Carbomer wherein the viscosity of the medium is pH-dependent;

b) adjusting the pH of the aqueous solution of a Carbomer until a gel with an apparent viscosity in the range 25 to 90 Pa.s at a shear rate of 1 $s^{-1}$ is reached;

c) allowing crystal growth;

d) adjusting the pH of the aqueous solution of a Carbomer until a fluid with an apparent viscosity less than 25 Pa.s at a shear rate of 1 $s^{-}1$ is reached; and e) harvesting the crystals.

6. Lactose monohydrate crystals obtained according to the process as claimed in claim 1.

7. A pharmaceutical formulation for administration by inhalation comprising lactose monohydrate crystals as claimed in claim 6.

8. A pharmaceutical formulation for administration by inhalation comprising lactose monohydrate crystals as claimed in claim 6 and/or fluticasone propionate or salmeterol xinafoate crystals.

9. A crystallisation process as claimed in claim 1, wherein the crystallised lactose monohydrate has an elongation ratio of 1.58±0.33 and a size in the range of 63 to 90 $\mu$m.

10. A lactose monohydrate according to claim 6, having an elongation ration of 1.58±0.33 and a size in the range of 63 to 90 $\mu$m.

11. Lactose monohydrate according to claim 6, having an elongation ratio from 1.55–2.20.

* * * * *